United States Patent [19]
Moriarty et al.

[11] Patent Number: 5,869,472
[45] Date of Patent: Feb. 9, 1999

[54] SYNTHESIS OF 1α-HYDROXY VITAMIN D

[75] Inventors: Robert M. Moriarty, Oak Park; Liang Guo; Raju A. Penmasta, both of Bolingbrook, all of Ill.

[73] Assignee: Bone Care International, Inc., Madison, Wis.

[21] Appl. No.: 776,283

[22] PCT Filed: Jul. 18, 1994

[86] PCT No.: PCT/US94/08002

§ 371 Date: Apr. 17, 1997

§ 102(e) Date: Apr. 17, 1997

[87] PCT Pub. No.: WO96/02501

PCT Pub. Date: Feb. 1, 1996

[51] Int. Cl.⁶ .......................... A61K 31/59; C07C 401/00
[52] U.S. Cl. ............................................. 514/167; 552/653
[58] Field of Search ............................... 552/653; 514/167

[56] References Cited

U.S. PATENT DOCUMENTS

| | | | |
|---|---|---|---|
| 3,880,894 | 4/1975 | DeLuca et al. | 552/653 |
| 3,907,843 | 9/1975 | DeLuca et al. | 552/653 |
| 3,966,777 | 6/1976 | Mazur et al. | 552/653 |
| 4,022,891 | 5/1977 | Takeshita et al. | 552/653 |
| 4,195,027 | 3/1980 | DeLuca et al. | 552/653 |
| 4,202,829 | 5/1980 | DeLuca et al. | 552/653 |
| 4,260,549 | 4/1981 | DeLuca et al. | 552/653 |
| 4,263,215 | 4/1981 | Hesse et al. | 552/653 |
| 4,265,822 | 5/1981 | DeLuca et al. | 552/653 |
| 4,338,250 | 7/1982 | DeLuca et al. | 552/653 |
| 4,554,105 | 11/1985 | Hesse | 552/653 |
| 4,554,106 | 11/1985 | DeLuca et al. | 552/653 |
| 4,555,364 | 11/1985 | DeLuca et al. | 552/653 |
| 4,670,190 | 6/1987 | Hesse et al. | 552/653 |
| 4,772,433 | 9/1988 | Hesse | 552/653 |
| 4,800,198 | 1/1989 | DeLuca et al. | 514/167 |
| 5,104,864 | 4/1992 | DeLuca et al. | 514/167 |
| 5,536,828 | 7/1996 | Deluca et al. | 540/95 |

FOREIGN PATENT DOCUMENTS

| | | |
|---|---|---|
| 0 078 704 | 5/1983 | European Pat. Off. . |
| 0 078 705 | 5/1983 | European Pat. Off. . |
| 2 108 793 | 4/1981 | United Kingdom . |
| 2 108 506 | 5/1983 | United Kingdom . |

OTHER PUBLICATIONS

E. Braunwald et al., "Disorders of Bone and Mineral Metabolism, Chpater 335," *Harrison's Principles of Internal Medicine: Part Eleven*, (eds.), McGraw–Hill. New York (1987) pp. 1860–1865.

E.G. Baggiolini et al., *J. Am. Chem. Soc.,* vol. 104 (1982) pp. 2945–2948.

D.R. Andrews et al., *J. Org. Chem.,* vol. 51 (1986) pp. 1635–1637.

*Primary Examiner*—Deborah C. Lambkin
*Attorney, Agent, or Firm*—Grady J. Frenchick; Karen B. King; Stroud, Stroud, Willink, Thompson & Howard

[57] ABSTRACT

A method for 1α-hydroxylation of vitamin D compounds using the appropriate vitamin D as the starting material. The method requires no separatory procedures prior to the actual hydroxylation step.

11 Claims, 2 Drawing Sheets

5,869,472

SYNTHESIS OF 1α-HYDROXY VITAMIN D

This application is a 371 of PCT/US94/08002 filed Jul. 18, 1994.

TECHNICAL FIELD

This invention relates generally to vitamin D compounds and their hydroxylated derivatives. More specifically, the invention relates to a novel synthesis of 1α-hydroxy vitamin D.

BACKGROUND OF THE INVENTION

The vitamins D are a group of compounds that are steroid derivatives and are known to be important in the regulation of calcium and phosphate metabolism in animals and man, and in the regulation of bone formation. See, *Harrison's Principles of Internal Medicine*: Part Eleven, "Disorders of Bone and Mineral Metabolism, Chapter 335," E. Braunwald et al., (eds.), McGraw-Hill, New York (1987) pp. 1860–1865.

The naturally occurring form of vitamin D in animals and man is vitamin $D_3$. Vitamin $D_3$ is synthesized endogenously in the skin of animals and man. The biological functions of vitamin D require metabolism to hydroxylated metabolites that are the biologically active agents. In animals, including man, vitamin $D_3$ is activated by being hydroxylated in the $C_{25}$ position in the liver, followed by 1α-hydroxylation in the kidney to produce the hormone 1α,25-dihydroxy vitamin $D_3$. See, U.S. Pat. No. 3,880,894 issued to DeLuca et al.

The 1α,25-dihydroxy vitamin $D_3$ compound regulates calcium and phosphorus metabolism, bone formation, and subsequent vitamin $D_3$ activation, by binding to specific cytoplasmic receptor proteins located throughout the body. This binding requires the presence of the 1α-hydroxy group. Hormonally active vitamin $D_3$ bound to intestinal receptors stimulates calcium and phosphate transport from the intestinal lumen into the systemic circulation. Activated vitamin $D_3$ bound to receptors in the parathyroid glands, the kidney, the osteoblasts, and other target tissues, elicits cellular responses which synergistically stabilize the levels of calcium and phosphorus in the blood, control the formation and removal of bone, and regulate further production of 1α,25-dihydroxy vitamin $D_3$. Vitamin $D_3$ has also been reported to play a role in cell proliferation and differentiation. See, U.S. Pat. No. 4,800,198 issued to DeLuca et al. It has been suggested that these compounds might be useful in the treatment of diseases characterized by abnormal cell proliferation and/or cell differentiation, such as leukemia, myelofibrosis and psoriasis.

Vitamin $D_2$ is the major naturally occurring form of vitamin D in plants. Vitamin $D_2$ differs structurally from vitamin $D_3$ by having a methyl group at $C_{24}$ and a double bond between $C_{22}$ and $C_{23}$. Various vitamin $D_2$ analogues, however, elicit strong physiological responses in animals and human beings, and are valuable substitutes for vitamin $D_3$ compounds.

Considerable interest has focused on the discovery and synthesis of various hydroxylated and dihydroxylated derivatives of vitamins D. As is generally understood and used herein, the term "vitamin D" is intended to include vitamins $D_3$, $D_2$, and $D_4$. Examples of hydroxylated and dihydroxylated metabolites of vitamins $D_3$ and $D_2$ which have been found to occur naturally and/or have been synthesized include 25-hydroxy vitamin $D_2$, 24, 25-dihydroxy vitamin $D_3$, 25, 26-dihydroxy vitamin $D_3$, 1α-hydroxy vitamin $D_2$, 23, 25-dihydroxy vitamin $D_3$, all of which have been found to exhibit vitamin D-like biological activity in vivo.

Unfortunately, while many of these active vitamin D metabolites held great promise as therapeutic agents, this promise has never been fully realized because of the extreme toxicity of these agents due to the well known potent effects of the compounds on calcium metabolism, giving rise to hypercalcemia in high doses. It has been reported, for example, that 1α-hydroxy vitamin $D_3$ at a daily dose of 2 μg/day (which has been shown in some studies to be effective in preventing loss of bone) causes toxicity in approximately 67 percent of patients. Recently, however, 1α-hydroxy vitamin $D_2$, has been shown to possess unexpectedly high biopotency and low toxicity. See, U.S. Pat. No. 5,104,864 issued to DeLuca et al. With this discovery, interest and need for straight forward, efficient syntheses of hydroxylated, particularly 1α-hydroxylated, vitamin D compounds has intensified.

Many methods of 1α-hydroxylation have been reported. Some of these methods use steroid starting materials that are first hydroxylated and then converted to the corresponding vitamin D compound. See, e.g., U.S. Pat. No. 4,670,190 issued to Hesse; U.S. Pat. No. 4,022,891 issued to Takeshita; U.S. Pat. No. 3,966,77 issued to Mazur; U.S. Pat. No. 3,907,843 issued to DeLuca et al. Others directly hydroxylate vitamin D compounds. See, e.g., U.S. Pat. No. 4,338,250 issued to DeLuca et al.; U.S. Pat. No. 4,202,829 issued to DeLuca et al.; U.S. Pat. No. 4,263,215 issued to Hesse et al.; U.S. Pat. No. 4,772,433 issued to Hesse; U.S. Pat. No. 4,554,105 issued to Hesse. Some proceed via a cyclovitamin. See, e.g., U.S. Pat. No. 4,555,364 issued to DeLuca et al.; U.S. Pat. No. 4,260,549 issued to DeLuca et al.; U.S. Pat. No. 4,195,027 issued to DeLuca et al. Still others provide a total synthesis of the desired vitamin D compound from simple precursors. See, e.g., Baggiolini et al., *J. Am. Chem. Soc.*, vol. 104 (1982) pp. 2945–48. Most produce poor yields of desired product. Each new synthesis claims to simplify those which came before. However, even those that claim to be simpler, more efficient methods still require considerable separatory steps, as, for example, by chromatography, in the synthesis.

Despite recognition of the need for a simple, straight forward method of producing hydroxylated vitamin D compounds, the art has yet to respond with such a method for the synthesis of 1α-hydroxy vitamin D.

SUMMARY OF THE INVENTION

The present invention responds to a heretofore unmet need by the prior art, and specifically to the inherent inadequacies of prior synthetic processes for preparing 1α-hydroxylated vitamin D compounds. The method of the present invention is distinguished by its simplicity in that it eliminates certain separatory steps characteristic of prior art processes.

The present invention provides a method of producing 1α-hydroxy vitamin D which includes the following steps: (a) forming 3-(protected-hydroxy) vitamin D from vitamin D; (b) forming a Diels-Alder adduct at $C_6$ and $C_{19}$ of the 3-(protected-hydroxy) vitamin D; (c) allylically oxidizing and decomposing the Diels-Alder adduct to form trans 1α-hydroxy-3-(protected-hydroxy) vitamin D; (d) irradiating the trans 1α-hydroxy-3-(protected-hydroxy) vitamin D to form cis 1α-hydroxy-3-(protected-hydroxy) vitamin D; and (e) deprotecting the cis 1α-hydroxy-3-(protected-hydroxy) vitamin D to form 1α-hydroxy vitamin D. Steps (a) and (b) are performed without purification of the resulting product of each step. The protecting step (a) preferably uses a trihydrocarbylsilyloxy reagent. The Diels-Alder reactant is preferably N-sulfinyl-p-toluenesulfonamide or selenium di-(p-toluenesulfonamide) while the allylically oxidizing step (c) is preferably accomplished with selenium dioxide and N-methyl morpholine N-oxide. The deprotecting step (e) preferably uses a quaternary ammonium fluoride.

The present method is applicable to any vitamin D derivative for which 1α-hydroxylation is desired, and thus, provides a flexibility in terms of starting material chosen and product. In particular, the method can be used advantageously for converting any of the known vitamin D metabolites to their 1α-hydroxy forms. The method of the present provides higher yields compared to the known synthesis utilizing a cyclovitamin intermediate and has fewer steps than that process. The method avoids the known maleic anhydride separation of cis and trans 1α-hydroxy vitamin D.

Other advantages and a fuller appreciation of the specific adaptations, compositional variations, and physical and chemical attributes of the present invention will be gained upon an examination of the following detailed description of the invention, taken in conjunction with the accompanying drawings and appended claims.

BRIEF DESCRIPTION OF THE DRAWINGS

The present invention will hereinafter be described in conjunction with the appended drawing, wherein like designations refer to like elements throughout and in which.

DETAILED DESCRIPTION

The present invention provides a synthetic route for 1α-hydroxy vitamin D, i.e., the compounds of general formula (I):

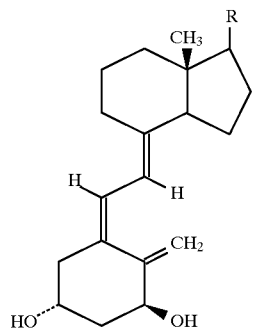

wherein R signifies any substituent that may be desired in the final product. Of primary interest are the steroid side chains that have at least 7 carbon atoms, and can be branched or unbranched, saturated or unsaturated, hetero-substituted or nonhetero-substituted, cyclic or noncyclic and which increase the serum calcium of the vitamin D deficient rat as determined by standard techniques used by biochemists in the vitamin D area. Examples of side chains are those where R represents the side chain of cholesterol or ergosterol or modified cholesterol or modified ergosterol side chains.

Among the preferred 1α-hydroxy vitamin D compounds of the present invention are those where is R has the formula:

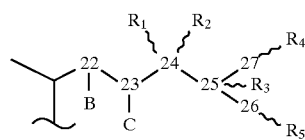

wherein B and C are either hydrogen or a carbon to carbon bond forming a double bond between $C_{22}$ and $C_{23}$; $R_1$, $R_3$, $R_4$ and $R_5$ are each independently hydrogen, hydroxy, lower alkyl, o-lower alkyl, o-lower acyl, o-aromatic acyl or fluoro; and $R_2$ is hydrogen or lower alkyl. Most preferred among the compounds of formula (I) are 1α-hydroxy vitamin $D_3$, 1α-hydroxy vitamin $D_2$, and 1α-hydroxy vitamin $D_4$.

In the formulae shown in this specification and in the claims, a wavy line to a substituent, e.g, to $R_1$, indicates that the substituent can exist in stereoisomeric alternate forms. As used herein the term "lower" as a modifier of alkyl or acyl is intended to identify a hydrocarbon radical in all isomeric forms, e.g., methyl, ethyl, butyl, formyl. As used herein, the term "protected-hydroxy" refers to a hydroxyl group in which the hydrogen has been replaced by a hydrocarbon or the like group, i.e., the hydroxyl group is present in derivatized form. A protected-hydroxyl group may include, e.g., O-alkyl, O-acyl, O-benzyloxycarbonyl, and O-alkylsilyl, preferably, trihydrocarbonylsilyloxy groups such as trimethylsilyloxy, n-butyldimethylsilyloxy, and most preferred, tertbutyldimethylsilyloxy.

Figure 1:
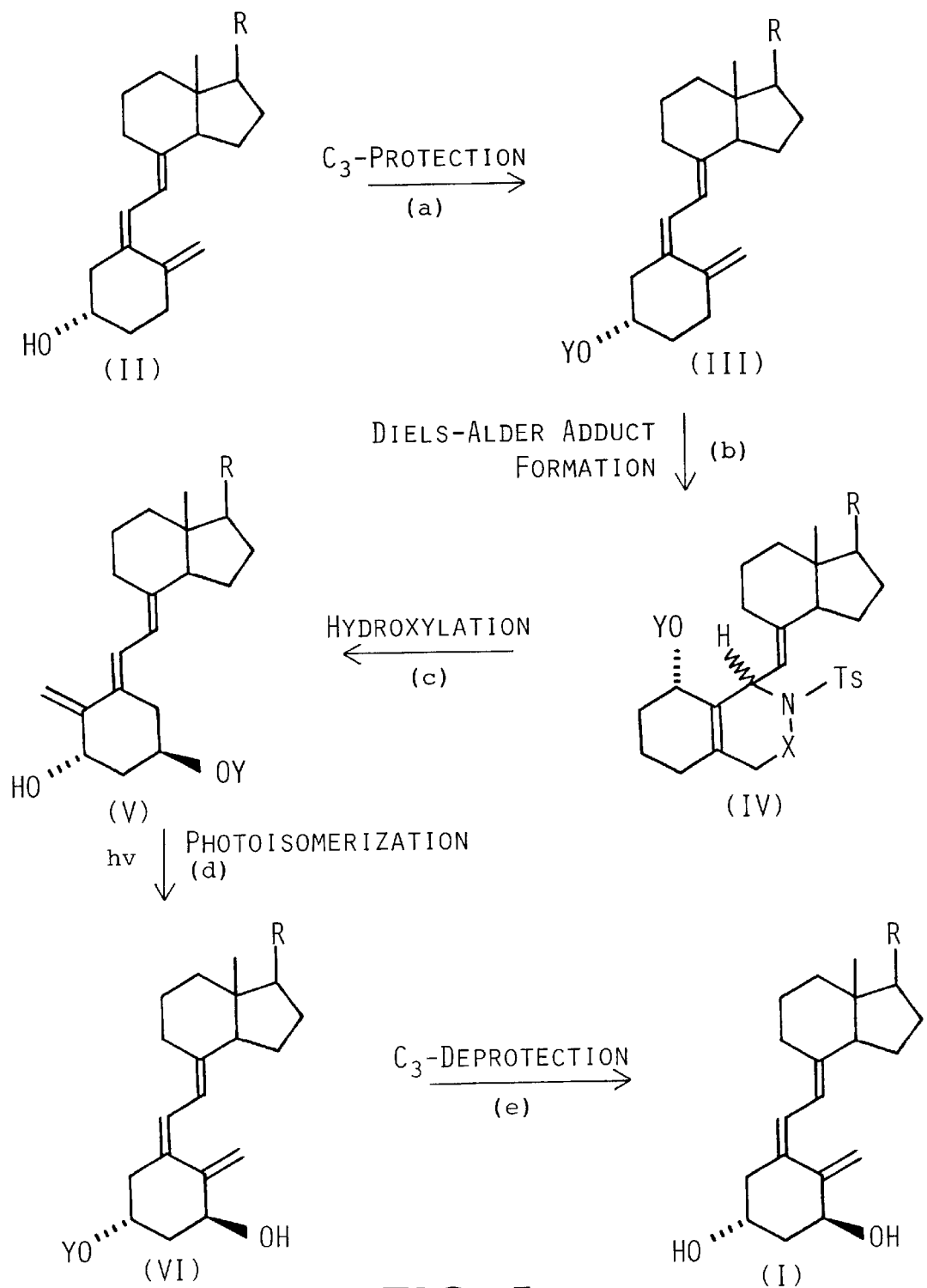
FIG. 1 illustrates the general schema for the synthesis of 1α-hydroxy-vitamin D starting with vitamin D.

The synthesis of 1α-hydroxy vitamin D (i.e., the compound of formula (I)) is accomplished according to the reaction scheme presented in FIG. 1. The synthesis uses a vitamin D compound, i.e., a compound of formula (II), as the starting material. Vitamin D first undergoes a protection step by applying a protected-hydroxy group to the $C_3$ position to yield the compound of formula (III). The protected-hydroxy group is preferably a trihydrocarbylsilyloxy group, most preferably tert-butyldimethylsilyloxy. The 3-(protected-hydroxy) vitamin D (III) is then subjected to a Diels-Alder reaction to form with $C_6$ and $C_{19}$ an adduct of formula (IV). The reagent for the Diels-Alder reaction is preferably an N-sulfinyl or an N-selenium derivative of tosylamide. The Diels-Alder adduct (IV) is then hydroxylated at the $C_1$ position to yield the trans 1α-hydroxy-3-(protected-hydroxy) vitamin D compound of formula (V). This trans compound is then subjected to photoisomerization to yield the cis 1α-hydroxy-3-(protected-hydroxy) compound of formula (VI). The cis protected-hydroxy compound (VI) is then deprotected to yield the 1α-hydroxy vitamin D of formula (I). It has been found that, unlike similar 1α-hydroxylation processes which use Diels-Alder adduct formation as an intermediate step (See, e.g., U.S. Pat. Nos. 4,554,105 and 4,772,433 to Hesse), the product of the protection step and the Diels-Alder adduct formation step do not require purification and can be used directly for the next step in the process. Thus, the method in accordance with the present invention requires no chromatographic or other separatory technique until the hydroxylation step is completed.

Figure 2:
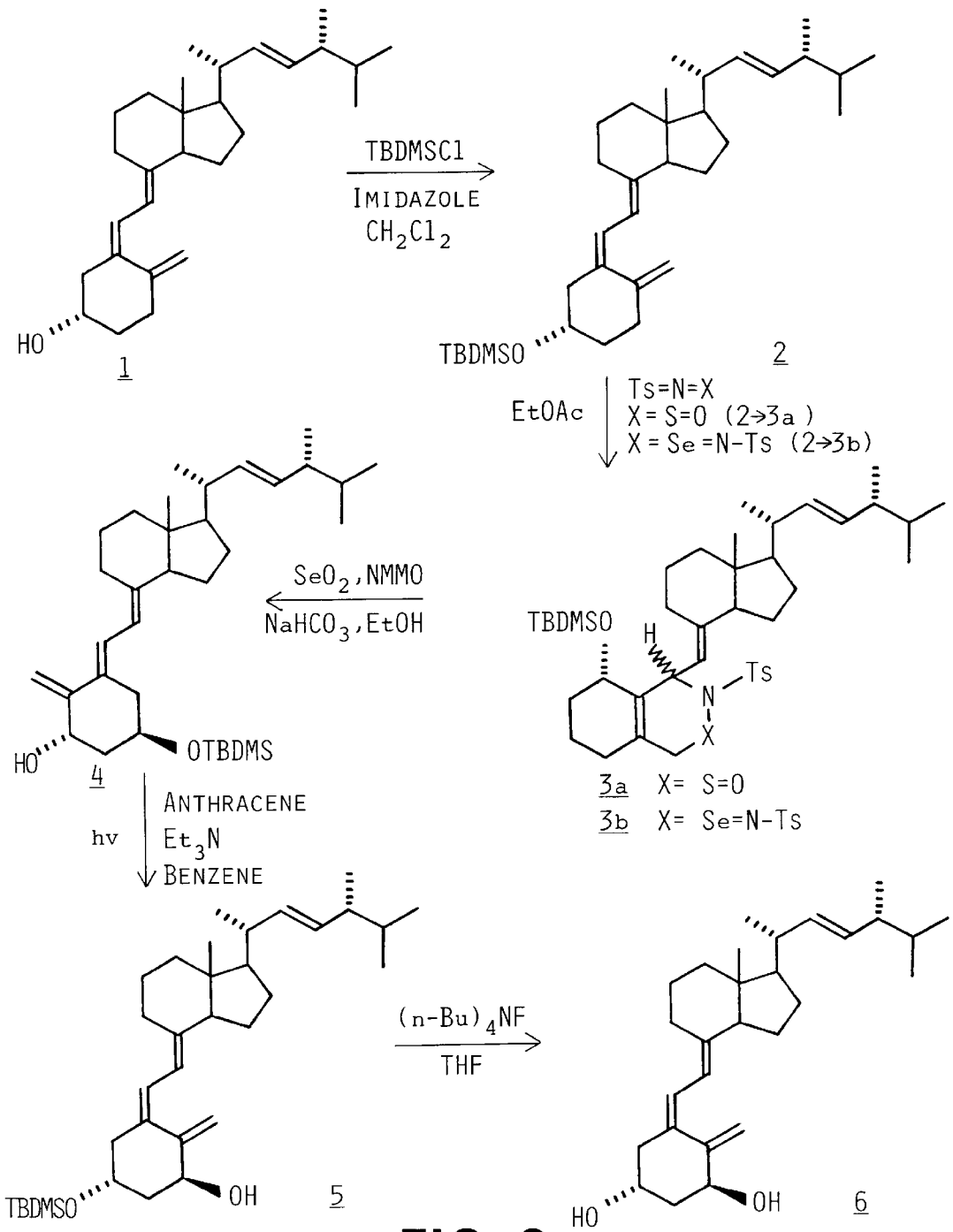
FIG. 2 illustrates the preparative steps for the synthesis of 1α-hydroxy-vitamin $D_2$ starting with vitamin $D_2$.

Reference is now made to FIG. 2, in which the synthesis of 1α-hydroxy vitamin $D_2$ (i.e., the compound of formula (6)) is specifically illustrated. Vitamin $D_2$ is reacted with tert-butyldimethylsilyloxychloride to protect the $C_3$ position, yielding 3-tert-butyldimethylsilyloxy vitamin $D_2$. The unpurified, crude product is then reacted with either N-sulfinyl-p-toluenesulfonamide (N-sulfinyl tosylamide; TsN=S=O) or selenium di-(p-toluenesulfonamide) (TsN=Se=NTs) as the Diels-Alder reagent to form an adduct at $C_6$ and $C_{19}$. The unpurified adduct is then hydroxylated by allylic oxidation at the $C_1$ position, with, e.g., selenium dioxide and co-oxidant N-methyl morpholine N-oxide, to form the trans 1α-hydroxy-3-tert-butyldimethylsilyloxy-vitamin $D_2$ while decomposing the adduct. The trans compound is then irradiated to form the cis compound which in turn is deprotected to return the hydroxy group with a quaternary ammonium fluoride such as tetra-n-butyl ammonium fluoride to yield 1α-hydroxy vitamin $D_2$.

The 1α-hydroxylated vitamin D compounds and analogues are medically useful as therapeutic agents for the treatment and prophylaxis of various human and animal diseases related to calcium imbalance, vitamin D deficiency, and bone loss.

The following examples are to be construed as merely illustrative, and not limitative of the remainder of the disclosure in any way whatsoever. In the following examples, all temperatures are set forth in degrees Celsius; unless otherwise indicated, all product yields are reported as percentages by weight. Proton nuclear magnetic resonance ($^1$H NMR) spectra were recorded with a Bruker AM-400 (400 MHz) with Aspect 3000 Computer in $CDCl_3$ solutions with $CHCl_3$ as an internal standard. Chemical shifts are reported in ppm. Infrared (IR) spectra were recorded with an IBM System 9000 FT-infrared spectrophotometer using samples as potassium bromide (KBr) pellets. Mass spectra (MS) were recorded with a Finnigan MAT-90 mass spectrometer at 20 eV/CI. Thin layer chromatography (TLC) was performed on silica gel with the solvents as indicated in each example. Melting points (mp) were determined with a Hoover-Thomas (capillary) Uni-Melt or a Fisher-Johns (cover slip-type) Melting Point apparatus.

EXAMPLE 1

Synthesis of 1α-Hydroxy Vitamin $D_2$
3-tert-butyldimethylsilyloxy Vitamin Do (2)):

A dichloromethane (100 ml) solution containing vitamin $D_2$ (1) (7.95 g, 20.0 mmol), tert-butyldimethylsilyloxyl ("TBDMS") chloride (4.56 g, 30.4 mmol) and imidazole (5.2 g, 76.5 mmol) was stirred at room temperature for 2 hours (monitored by TLC, 10% ethyl acetate in hexane). At the end of this time the reaction mixture was diluted with 500 ml of dichloromethane and washed with water (200 ml), 10% hydrochloric acid (200 ml), sat. NaCl (200 ml) and water (200 ml). The dichloromethane solution was dried over anhydrous $MgSO_4$ and evaporated to dryness under reduced pressure. TLC (5% ethyl acetate in hexane) showed almost quantitative conversion to the 3-TBDMS vitamin $D_2$. The crude product 3-TBDMS vitamin $D_2$ (2), (~11 g), was used for a Diels-Alder reaction (step 2) without further purification.
TLC (5% ethyl acetate in hexane): $R_f$=0.70
IR (KBr): strong CH stretching ~2959 $cm^{-1}$.
MS (CI): 511(M+1)(100%),379(65).
$^1$H NMR (400 MHz): δ 6.18 (1H, d, 6-H), 6.02 (1H, d, 7-H), 5.21 (2H, m, 22,23-H, 5.01 (1H, s, 19-H), 3.85 (1H, m, 3-H), 1.03 (3H, d, 28-H), 0.93 (3H, d, 21-H), 0.90 (9H, s, t-Bu), 0.85 (6H, t, 26, 27-H), 0.58 (3H, s, 18-H), 0.08 (3H, s., Si—Me), 0.07 (3H, s, Si—Me).
Diels-Alder Adduct of 3-tert-butyldimethylsilyloxy vitamin $D_2$ (3a):

To a stirred solution of 3-TBDMS vitamin $D_2$ (2) (5.0 g, 9.8 mmol) from step (1) in 100 ml of anhydrous ethyl acetate was added N-sulfinyl-p-toluenesulfonamide (TsN=S=O) (2.56 g, 10.3 mmol). The reaction solution was stirred under $N_2$ at room temperature for 1 hour and monitored by TLC (20% ethyl acetate in hexane) for the complete consumption of the starting material (2). Then the solvent (ethyl acetate) was removed under reduced pressure to yield a crude product adduct (3a). The crude product was used for the hydroxylation without purification.
TLC (20% ethyl acetate in hexane): $R_f$=0.28
IR (KBr): strong CH stretching -2959 $cm^{-1}$, $SO_2$ stretching 1498, 1302 $cm^{-1}$.
$^1$H NMR (400 MHz): δ 7.80 (2H, d, aromatic), 7.42 (2H, d, aromatic), 5.21 (2H, m, 22, 23-H), 4.80 1H, m), 3.95 (1H, m, 3-H), 3.65 (1H, m), 3.28 (1H, m), 2.45 (3H, s, Me), 1.03 (3H, d, 28-H), 0.93 (3H, d, 21-H), 0.90 (9H, s, t-Bu), 0.85 (6H, t, 26, 27-H), 0.58 (3H, s, 18-H), 0.08 (3H, s, Si—Me), 0.07 (3H, s, Si—Me).
Diels-Alder Adduct of 3-tert-butyldimethylsilyloxy Vitamin $D_2$ (3b);

To a stirred solution of 3-TBDMS vitamin $D_2$ (2) (5.0 g, 9.8 mmol) in 100 ml of anhydrous dichloromethane was added TsN=Se=NTs (2.56 g, 10.3 mmol). The reaction solution was stirred under $N_2$ at room temperature for 12 hours and monitored by TLC (20% ethyl acetate in hexane) for the consumption of the starting material (2). Then the solvent (dichloromethane) was removed under reduced pressure to yield a crude product adduct (3b). The crude product was used for the hydroxylation step without purification.
TLC (20% ethyl acetate in hexane): $R_f$=0.54
IR (KBr): strong CH stretching ~2959 $cm^{-1}$, $SO_2$ stretching 1487, 1285 $cm^{-1}$.
$^1$H NMR (400 MHz): δ 7.80 (2H, d, aromatic), 7.42 (2H, d, aromatic), 5.21 (2H, m, 22, 23-H), 4.80 (1H, m), 3.95 (2H, m), 3.85 (1H, m), 3.28 (1H, m), 2.45 (3H, s, Me), 1.03 (3H, d, 28-H), 0.93 (3H, d, 21-H), 0.90 (9H, s, t-Bu), 0.85 (6H, t, 26, 27-H), 0.58 (3H, s, 18-H), 0.08 (3H, s, Si—Me), 0.07 (3H, s, Si—Me).
trans 1α-Hydroxy-3-tert-butyldimethylsilyloxy-Vitamin $D_2$ (4):

To a solution of selenium dioxide (1.30 g, 11.6 mmol) in 200 ml of anhydrous ethyl alcohol was added N-methyl morpholine oxide (13.0 g, 111.1 mmol) and sodium bicarbonate (10.0 g, 119.0 mmol). Then the reaction solution was warmed to 55°~60° C. The Diels-Alder adduct (3a or 3b) (7.5 g) dissolved in 50 ml dry dichloromethane was then added to the solution. The reaction was stirred at 55°–60° C. for 1 hour under $N_2$ (monitored by TLC, 20% ethyl acetate in hexane). Then most of the ethyl alcohol was removed under reduced pressure. The reaction mixture was diluted with 1600 ml of ether. The ether solution was washed with water (500 ml). The aqueous layer was extracted with ether (500 ml). The combined ether solution was washed in sequence with 10% HCl (2×500 ml), NaCl (saturated) (2×500 ml) and water (500 ml) then dried over $MgSO_4$. The crude product was purified by column chromatography on silica gel (200 mesh; 10% ethyl acetate in hexane) to give 2.4 g of trans 1α-hydroxy-3-TBDMS vitamin $D_2$ (4) as a solid.
TLC (5% ethyl acetate in hexane): $R_f$=0.10
IR (KBr): strong OH stretching ~3413 $cm^{-1}$, strong CH stretching -2959 $cm^{-1}$.
MS (Cl): 527(M+1)(69%), 395(100).
$^1$H NMR (400 MHz): δ 6.53 (1H, d, 6-H), 5.88 (1H, d, 7-H) 5.20 (2H, m, 22, 23-H), 5.09 (1H, s, 19-H), 4.52 (1H, m, 3-H), 4.20 (1H, m, 3-H), 1.04 (3H, d, 28-H), 0.91 (3H, d, 21-H), 0.85 (9H, s, t-Bu), 0.80 (6H, t, 26, 27-H), 0.58 (3H, s, 18-H), 0.10 (6H, s, Si—Me).
1α-Hydroxy-3-tert-butyldimethylsilyloxy Vitamin $D_2$ (5)

A solution of the trans 1α-hydroxy-3-TBDMS Vitamin $D_2$ (2.3 g, 437 mmol) from step (3) in benzene (500 ml) containing triethylamine (1 ml) and anthracene (0.50 g, 2.81 mmol) was thoroughly degassed. A Hanovia UV Lamp ($\lambda_{max}$ 360 nm) was placed such that the outside of the water cooled jacket was 15 cm from the reaction vessel. The solution was irradiated for 2 hours. Then solvent was removed under the reduced pressure. The crude product was purified by column chromatography (5% ethyl acetate in hexane) to give 1.3 g of cis 1α-hydroxy-3-TBDMS Vitamin $D_2$ (5).

TLC (5% ethyl acetate in hexane): $R_f$=0.20
IR (KBr): strong OH stretching ~3400 cm$^{-1}$, strong CH stretching ~2959 cm$^{-1}$.
MS (Cl): 413 (M+1) (24%), 395 (M=1-$H_2$)) (100), 377 (M+1-2$H_2$O) (27%).
$^1$H NMR (400 MHz): δ 6.35 (1H, d, 6-H), 6.05 (1H, d, 7-H), 5.28 (2H, m, 22, 23-H), 5.20 (1H, s, 19-H), 4.99 (1H, s, 19-H), 4.44 (1H, m, 1-H), 4.20 (1H, m, 3-H), 1.05 (3H, d, 28-H), 0.96 (3H, d, 21-H), 0.90 (9H, s, t-Bu), 0.86 (6H, t, 26, 27-H), 0.58 (3H, s, 18-H), 0.09 (3H, s, Si—Me), 0.04 (3H, s, Si—Me).

Cis 1α-Hydroxy-Vitamin $D_2$ (6):

To a stirred solution of cis 3-TBDMS-1α-hydroxy-vitamin $D_2$ (5) (0.9 g, 171 mmol) from step (4) in 50 ml of tetrahydrofuran (THF) was added n-butylammonium fluoride (1M solution in THF, 5 ml, 5.00 mmol). The resulting solution was stirred at room temperature for 13 hours (monitored by TLC, 40% ethyl acetate in hexane). Then most of the THF was removed under reduced pressure. The residue was diluted with 300 ml of ethyl acetate. The ethyl acetate solution was washed with water (2×100 ml), dried over anhydrous $MgSO_4$, concentrated under reduced pressure. The crude product was purified by column chromatography on silica gel (40% ethyl acetate in hexane) to give 0.51 g of cis 1α-hydroxyvitamin $D_2$ (6).

mp: 153°–155° C. (from methyl formate) (Literature value: 138°–140° C.)
IR (KBr): strong OH stretching ~3420 cm$^{-1}$, strong CH stretching ~2959 cm$^{-1}$.
MS (Cl): 413(M+1)(24%), 395(M+1-$H_2$)(100), 377(M+1-2$H_2$O) (27%).
$^1$H NMR (400 MHz): δ 6.38 (1H, d, 6-H), 6.02 (1H, d, 7-H), 5.33 (1H, s, 19-H), 5.21 (2H, m, 22, 23-H), 5.00 (1H, s, 19-H), 4.42 (1H, m, 1-H), 4.23 (1H, m, 3-H), 1.02 (3H, d, 28-H), 0.92 (3H, d, 21-H), 0.83 (6H, t, 26, 27-H), 0.56 (3H, s, 18-H).

The material of melting point 153°–155° C. was identical in all respects with a reference sample prepared by a known method. Using this procedure starting with 25 g of vitamin $D_2$, 5 g of cis 1α-hydroxy vitamin $D_2$ was obtained. Utilizing procedures similar to described above, substituting other vitamin D compounds as starting materials, e.g., vitamin $D_3$, vitamin $D_4$, 25-hydroxy vitamin $D_3$, 24, 25-dihydroxy vitamin $D_3$, 25, 26-dihydroxy vitamin $D_3$, there is obtained their 1α-hydroxylated derivative. The 1α-hydroxylated compounds of the present invention are particularly advantageous for application as effective therapeutic agents in human and veterinary medicine, such as for the treatment of calcium and mineral imbalance conditions, and vitamin D responsive bone diseases, since the presence of a 1α-hydroxy group enhances the activity and efficacy of the vitamin.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method of producing 1α-hydroxy vitamin $D_2$, comprising subjecting 3-trihydrocarbylsilyloxy vitamin D to a Diels-Alder reaction forming 6,19 adduct; hydroxylating the adduct to form trans 1α-hydroxy-3-trihydrocarbosilyloxy vitamin D; isomerizing and deprotecting the trans 1α-hydroxy-3-trihydrocarbosilyloxy vitamin D to form 1α-hydroxy vitamin D.

2. A method of producing 1α-hydroxy vitamin D, comprising:
    (a) forming 3-(protected-hydroxy) vitamin D from vitamin D;
    (b) forming a Diels-Alder adduct at $C_6$ and $C_{19}$ of said 3-(protected-hydroxy) vitamin D without purifying said 3-(protected-hydroxy) vitamin D from step (a);
    (c) allylically oxidizing and decomposing said Diels-Alder adduct to form trans 1α-hydroxy-3-(protected-hydroxy) vitamin D without purifying said adduct from step (b);
    (d) irradiating the trans 1α-hydroxy-3-(protected hydroxy) vitamin D to form cis 1α-hydroxy-3-(protected-hydroxy) vitamin D; and
    (e) deprotecting the cis 1α-hydroxy-3-(protected-hydroxy) vitamin D to form 1α-hydroxy vitamin D.

3. The method of claim 2, wherein said allylically oxidizing step (c) is accomplished is with selenium dioxide and N-methyl morpholine N-oxide.

4. The method of claim 2, wherein said deprotecting step (e) uses a quaternary ammonium fluoride.

5. A method of preparing 1α-hydroxy vitamin D, comprising:
    (a) protecting vitamin D with a trihydroxcarbylsilyloxy group at $C_3$ to form 3-trihydrocarbylsilyloxy vitamin D;
    (b) reacting the 3-trihydrocarbylsilyloxy vitamin D with a Diels-Alder reactant to form 3-trihydrocarbylsilyloxy-vitamin D-6,19 adduct;
    (c) allylically oxidizing the adduct to form trans 1α-hydroxy-3-trihydrocarbylsilyloxy vitamin D;
    (d) irradiating trans 1α-hydroxy-3-trihydrocarbylsilyloxy vitamin D to form cis 1α-hydroxy-3-trihydrocarbylsilyloxy vitamin D; and
    (e) deprotecting the cis 1α-hydroxy-3-trihydrocarbylsilyloxy vitamin D to form 1α-hydroxy vitamin D.

6. The method of claim 5, wherein steps (a) and (b) require no purification step.

7. The method of claim 5, wherein said Diels-Alder reactant is N-sulfinyl-p-toluenesulfonamide or selenium di-(p-toluenesulfonamide).

8. The method of claim 5, wherein said trihydroxcarbylsilyloxy group is tert-butyldimethylsilyloxy.

9. A method of preparing a Diels-Alder-$C_6/C_{19}$ adduct of vitamin D, comprising: reacting 3-tert-butyldimethylsilyloxy vitamin D with a Diels-Alder reactant wherein said Diels-Alder reactant is N-sulfinyl-p-toluenesulfonamide or selenium di-(p-toluenesulfonamide).

10. A method of producing 1α-hydroxy vitamin $D_2$, comprising deprotecting 1α-hydroxy-3-trihydrocarbylsilyloxy vitamin D with tetra-n-butylammonium fluoride to form 1α-hydroxy vitamin $D_2$.

11. A method for preventing or reversing bone loss or bone demineralization, comprising:
    (a) forming 3-(protected-hydroxy) vitamin D from vitamin $D_2$;

(b) forming a Diels-Alder adduct at $C_6$ and $C_{19}$ of said 3-(protected-hydroxy) vitamin $D_2$ without purifying said 3-(protected-hydroxy) vitamin $D_2$ from step (a);

(c) allylically oxidizing and decomposing said Diels-Alder adduct to form trans 1α-hydroxy-3-(protected-hydroxy) vitamin $D_2$ without purifying said adduct from step (b);

(d) irradiating the trans 1α-hydroxy-3-(protected-hydroxy) vitamin $D_2$ to form cis 1α-hydroxy-3-(protected-hydroxy) vitamin $D_2$;

(e) deprotecting the cis 1α-hydroxy-3-(protected-hydroxy) vitamin $D_2$ to form 1α-hydroxy vitamin $D_2$.

(f) purifying said 1α-hydroxy vitamin $D_2$; and (g) administering an amount of said 1α-hydroxy-vitamin $D_2$ to a patient suffering from or predisposed to bone loss or bone demineralization effective to prevent or stabilize the bone loss or demineralization.

* * * * *

UNITED STATES PATENT AND TRADEMARK OFFICE
CERTIFICATE OF CORRECTION

PATENT NO. : 5,869,472
DATED : February 9, 1999
INVENTOR(S) : Robert M. Moriarty, Liang Guo, and Raju A. Penmasta It is certified that error appears in the above-indentified patent and that said Letters Patent is hereby corrected as shown below:

Col. 3, lines 12-13, "the present provides" should read --the present invention provides--.

Col. 3, line 66, "where is R has" should read --where R has--.

Col. 4, line 25, "O-alkyl, O-acyl, O-benzyloxycarbonyl" should read --o-alkyl, o-acyl, o-benzyloxycarbonyl--.

Col. 5, line 36, "(2)):" should read --(2):--.

Col. 5, line 53, "-2959" should read --~2959--.

Col. 6, line 6, "-2959" should read --~2959--.

Col. 6, line 57, "-2959" should read --~2959--.

Col. 10, line 2, "vitamin $D_2$." should read --vitamin $D_2$;--.

Signed and Sealed this

Seventeenth Day of August, 1999

Q. TODD DICKINSON

Attest:

Attesting Officer

Acting Commissioner of Patents and Trademarks